(12) United States Patent
Suzuki et al.

(10) Patent No.: US 11,273,094 B2
(45) Date of Patent: Mar. 15, 2022

(54) CUPSOLE, WALKING ASSISTANCE APPARATUS, INDEX MEMBER, AND CUPSOLE ATTACHING METHOD

(71) Applicant: TOYOTA JIDOSHA KABUSHIKI KAISHA, Toyota (JP)

(72) Inventors: Kanako Suzuki, Toyota (JP); Yoshinori Fujikake, Nagakute (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 266 days.

(21) Appl. No.: 15/924,727

(22) Filed: Mar. 19, 2018

(65) Prior Publication Data
US 2018/0289578 A1 Oct. 11, 2018

(30) Foreign Application Priority Data
Apr. 10, 2017 (JP) .............................. JP2017-077555

(51) Int. Cl.
*A61H 3/00* (2006.01)
*A61H 1/02* (2006.01)
*A61F 5/01* (2006.01)

(52) U.S. Cl.
CPC ............ *A61H 3/00* (2013.01); *A61F 5/0195* (2013.01); *A61H 1/0262* (2013.01); *A61H 2201/0192* (2013.01); *A61H 2201/164* (2013.01); *A61H 2201/165* (2013.01); *A61H 2201/1642* (2013.01); *A61H 2201/1645* (2013.01); *A61H 2201/1647* (2013.01); *A61H 2201/5064* (2013.01); *A61H 2205/12* (2013.01)

(58) Field of Classification Search
CPC .................. A61H 3/00; A61H 1/0262; A61H 2201/0192; A61H 2201/164; A61H 2201/1642; A61H 2201/1645; A61H 2201/1647; A61H 2201/165; A61H 2201/5064; A61H 2205/12; A61F 5/0195
USPC ......................................................... 601/34
See application file for complete search history.

(56) References Cited

U.S. PATENT DOCUMENTS

| | | | |
|---|---|---|---|
| 2,131,401 A * | 9/1938 | Karlen | B42F 13/08 402/18 |
| 9,510,965 B2 * | 12/2016 | Grim | A61F 5/0111 |
| 2008/0125294 A1 * | 5/2008 | Takizawa | A61H 1/024 482/92 |
| 2010/0218400 A1 | 9/2010 | Klatt et al. | |
| 2011/0021963 A1 | 1/2011 | Graddon et al. | |

(Continued)

FOREIGN PATENT DOCUMENTS

| | | |
|---|---|---|
| JP | 5-123204 | 5/1993 |
| JP | 2014-188037 | 10/2014 |

(Continued)

*Primary Examiner* — Timothy A Stanis
*Assistant Examiner* — Benjamin M. Kusiak
(74) *Attorney, Agent, or Firm* — Oblon, McClelland, Maier & Neustadt, L.L.P.

(57) ABSTRACT

A cupsole, that a user wears and is fixed to a foot sole plate of a walking assistance apparatus that assists a motion of a leg part of the user, includes: a main body part on which the user's foot is placed; and an index member that is fixed to the main body part and is configured to determine an attachment position with respect to a reference index provided in the foot sole plate, the attachment position varying for each user, in which the index member can be attached to or detached from the main body part.

7 Claims, 8 Drawing Sheets

(56) References Cited

U.S. PATENT DOCUMENTS

| | | | |
|---|---|---|---|
| 2012/0116275 A1* | 5/2012 | Pochatko | A61F 5/0111 602/13 |
| 2012/0232438 A1* | 9/2012 | Cataldi | A61H 1/0259 601/5 |
| 2013/0074363 A1* | 3/2013 | Adams | A43B 1/0027 36/7.1 R |
| 2013/0122292 A1 | 5/2013 | Carrdine | |
| 2014/0109440 A1* | 4/2014 | McDowell | A43B 3/246 36/103 |
| 2015/0290074 A1* | 10/2015 | Koenig | A43B 3/0031 601/46 |
| 2016/0067077 A1* | 3/2016 | Li | A61F 5/0127 602/28 |
| 2016/0270997 A1 | 9/2016 | Little et al. | |
| 2017/0049601 A1 | 2/2017 | Willard | |
| 2018/0325713 A1* | 11/2018 | Gregg | A61F 5/0102 |

FOREIGN PATENT DOCUMENTS

| | | |
|---|---|---|
| JP | 2017-148172 A | 8/2017 |
| WO | WO 2016/116649 A1 | 7/2016 |

\* cited by examiner

CUPSOLE, WALKING ASSISTANCE APPARATUS, INDEX MEMBER, AND CUPSOLE ATTACHING METHOD

CROSS REFERENCE TO RELATED APPLICATIONS

This application is based upon and claims the benefit of priority from Japanese patent application No. 2017-77555, filed on Apr. 10, 2017, the disclosure of which is incorporated herein in its entirety by reference.

BACKGROUND

This disclosure relates to a cupsole, a walking assistance apparatus, an index member, and a cupsole attaching method.

A walking assistance apparatus that is mounted on a leg part of a user and assists the user's walking has been known. For example, a walking assistance apparatus disclosed in Japanese Unexamined Patent Application Publication No. 2014-188037 couples together a lower thigh frame mounted on a lower thigh part of a user and a placement part on which the user places his/her sole in such a way that they can be rotated relative to each other.

SUMMARY

A shoe-shaped cupsole may be used in order to fix a user's foot on a placement part of a walking assistance apparatus. The walking assistance apparatus may be shared among a plurality of users, and a user who is going to use the walking assistance apparatus needs to adjust the optimal position of the cupsole on the placement part every time he/she uses this apparatus. While it may be possible for each user to have his/her own cupsole and record information on the optimal position in his/her own cupsole, this causes a problem that a cost increases. That is, it is difficult to meet both the demand for sharing various mounting tools as much as possible and the demand for omitting troublesome work required when the user starts using the walking assistance apparatus.

This disclosure has been made in order to solve the aforementioned problems and aims to provide a cupsole and the like that do not require troublesome work when the user starts using the walking assistance apparatus while allowing users to share the mounting tools as much as possible.

A cupsole according to a first aspect of the present disclosure is a cupsole that a user wears and is fixed to a foot sole plate of a walking assistance apparatus that assists a motion of a leg part of the user, the cupsole including: a main body part on which the user's foot is placed; and an index member that is fixed to the main body part and is configured to determine an attachment position with respect to a reference index provided in the foot sole plate, the attachment position varying for each user, in which the index member can be attached to or detached from the main body part.

According to the aforementioned structure, the index member can be attached to or detached from the main body part of the cupsole, whereby only the index member may be owned by each user and the cupsole can be shared among users. Further, since the positional information on the cupsole with respect to the reference index of the foot sole plate can be recorded in the index member, when the user uses the walking assistance apparatus for the second and subsequent times, the user only needs to mount the index member on the main body part and perform simple adjustment, thereby being able to start using the walking assistance apparatus.

In the aforementioned cupsole, the index member may be a translucent member that overlaps the reference index when the index member is used, and is able to mark a personal index of the user with respect to the reference index. By using the translucent member, the user can form a mark with, for example, a pen while visually recognizing the reference index, whereby it is possible to easily record the positional information for each user.

In this case, the index member includes two or more mounting parts to be mounted on the main body part, in which the main body part includes mounted parts that correspond to the respective mounting parts, and the mounting parts and the mounted parts are arranged in such a way that the index member cannot be attached to the main body part by combinations other than a given combination. According to the aforementioned structure, the mounting parts and the mounted parts are provided in such a way that they are rotationally asymmetrical, whereby the index member is not mounted on the main body part in a wrong direction.

Specifically, each of the mounting parts preferably includes an arm part that is extended from an index surface of the index member and each of the mounted parts preferably includes a hole part through which the arm part penetrates. According to this structure, the index member can be formed in a simple shape, and therefore it can be easily manufactured. In this case, the arm part may include a penetrating part that penetrates through the hole part and an extended part that is extended along the surface of the main body part after the penetrating part penetrates through the hole part. By providing this extended part, the index member can be mounted on the main body part in a stable manner.

Further, the main body part may include a window part that is smaller than the index surface provided in a position of the main body part that corresponds to an index surface of the index member. By providing the window part having the aforementioned structure, the user is able to visually recognize the reference index from the window part and to easily record the positional information such as a marking with respect to the index surface supported at the peripheral part of the window part.

Further, the index member is preferably provided in the part of the main body part that corresponds to the arch of the foot. When the index member is present at the position of the arch of the foot, the user's feeling of strangeness when the user uses the walking assistance apparatus can be reduced. In a similar way, an index surface of the index member may be provided in such a way that it is extended along an outer surface of the main body part, which is opposite to an inner surface of the main body part on which the user's foot is placed. Even with this structure, it is possible to reduce the user's feeling of strangeness. Further, the index member may be provided in an outer peripheral part of the main body part. When the index member is provided in the outer peripheral part of the main body part, the index member does not touch the user's foot. Therefore, the user does not have a feeling of strangeness.

A walking assistance apparatus according to a second aspect of the present disclosure is a walking assistance apparatus that assists a motion of a leg part of a user, the walking assistance apparatus including a foot sole plate configured to fix the aforementioned cupsole, in which the foot sole plate includes a reference index on which the index member overlaps. According to the walking assistance apparatus that can use the aforementioned cupsole, the effects similar to those stated above can be obtained.

An index member according to a third aspect of the present disclosure is an index member that is mounted on a main body part of a cupsole, a user's foot being placed on the main body part, the cupsole being worn by the user and being fixed to a foot sole plate of a walking assistance apparatus that is mounted on a leg part of the user and assists a motion of the leg part of the user, the index member being mounted on the main body part in such a way that the index member can be attached to or detached from the main body part in order to determine an attachment position of the cupsole with respect to a reference index provided in the foot sole plate, the attachment position of the cupsole varying for each user. According to the aforementioned index member, the index member is used together with the main body part of the cupsole on which the index member is mounted, whereby it is possible to obtain the aforementioned effects.

A cupsole attaching method according to a fourth aspect of the present disclosure is a cupsole attaching method for attaching a cupsole worn by a user to a walking assistance apparatus that assists a motion of a leg part of the user, an attachment position of the cupsole varying for each user, the cupsole attaching method including: a mark forming step for adjusting a position of the cupsole on which an index member formed of a translucent member is mounted with respect to a reference index provided in a foot sole plate of the walking assistance apparatus to provide a personal index that matches the reference index on the translucent member; in a stage in which the user uses the walking assistance apparatus, a mounting step for mounting the translucent member on the cupsole; and an attaching step for causing the personal index provided in the mark forming step to match the reference index to determine the attachment position, thereby attaching the cupsole on which the translucent member has been mounted in the mounting step to the foot sole plate.

According to the aforementioned cupsole attaching method, only the index member may be owned by each user and the cupsole can be shared among users. Further, when the user uses the walking assistance apparatus for the second and subsequent times, the user can start using the walking assistance apparatus by just mounting the index member on the main body part and performing simple adjustment.

According to this disclosure, it is possible to provide a cupsole and the like that do not require troublesome work when the user starts using the walking assistance apparatus while allowing users to share the mounting tools as much as possible.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

While the present disclosure will be explained with reference to an embodiment of the present disclosure, the present disclosure set forth in claims is not limited to the following embodiment. Further, not all the structures explained in the embodiment are necessary as means for solving the problems.

Figure 1:
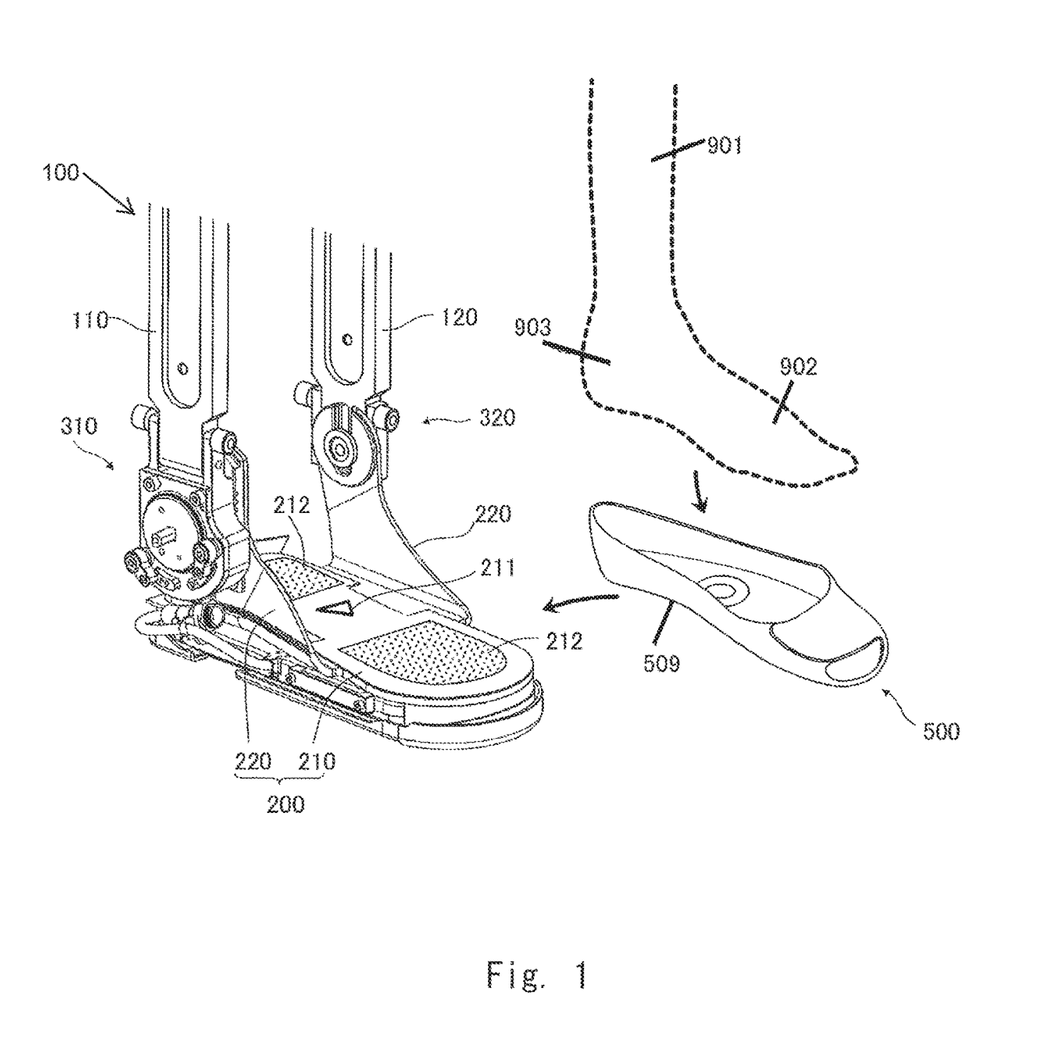
FIG. 1 is a diagram for describing a cupsole and a walking assistance apparatus according to an embodiment.

FIG. 1 is a diagram for describing a cupsole 500 and a walking assistance apparatus 100 according to this embodiment. The walking assistance apparatus 100 is an apparatus configured to assist walking by a user, who is a disabled person suffering from, for example, hemiplegia or an elderly person whose leg strength has been reduced. As one kind of walking assistance, for example, the movable range of an ankle joint 903 of the person who wears the walking assistance apparatus 100 is regulated. The walking assistance apparatus 100 is mainly composed of a lower thigh frame 110 configured to support a lower thigh 901, a sole frame 200 configured to support a foot 902 extended from the ankle, and a joint mechanism 310 configured to support the two frames in such a way that these frames can swing in a range regulated along the movable direction of the ankle joint 903.

The sole frame 200 includes a bottom plate 210, which serves as a foot sole plate having a placement surface on which the cupsole 500 is placed, and a side plate 220 installed on the side of the bottom plate 210. More specifically, the joint mechanism 310 couples together the lower end of the lower thigh frame 110 and the outer side plate 220 in such a way that they can swing. The joint mechanism 310 has a structure in which it swings in a range narrower than a range in which the ankle joint 903 can be originally bent in terms of the body structure.

The walking assistance apparatus 100 further includes a lower thigh frame 120 in such a way that the lower thigh frame 120 is opposed to the lower thigh frame 110 with the lower thigh 901 interposed therebetween. That is, the lower thigh frames 110 and 120 are mounted on the lower thigh 901 in such a way that they hold the lower thigh 901 therebetween, and support the lower thigh 901. The lower thigh frames 110 and 120 are mounted on the lower thigh 901 via a mounting belt (not shown).

The walking assistance apparatus 100 includes a joint mechanism 320 that couples together the lower thigh frame 120 and the inner side plate 220 in such a way that they can swing in a flexible manner. The joint mechanism 320 does not have a structure that regulates the swing like the joint mechanism 310. That is, the movable range of the ankle joint 903 is not regulated by the joint mechanism 320 provided in the inner side of the ankle joint 903. Instead, it is regulated by the joint mechanism 310 provided in the outer side of the ankle joint 903.

FIG. 1 assumes a case in which the affected leg is the right leg and the joint mechanism 310 is arranged in the outer side of the right leg. In this embodiment, the walking assistance apparatus 100 is a walking assistance apparatus for the right leg, and the cupsole 500 used for this walking assistance apparatus is also for the right leg. It is needless to say, however, that a walking training apparatus for the left leg may also be manufactured, and a cupsole for the left leg that is used in the walking training apparatus for the left leg may be manufactured as well.

The cupsole 500 forms a shoe shape and accommodates the foot 902. The main part of the cupsole 500 is formed of, for example, resin. A surface fastener 509 is bonded to the rear surface side of the cupsole 500, and the surface fastener 509 overlaps a surface fastener 212 bonded to the surface of the bottom plate 210, whereby the cupsole 500 is fixed to the sole frame 200. The method of fixing the cupsole 500 to the sole frame 200 is not limited to the surface fastener and another method may instead be used. For example, the four corners of the cupsole 500 may be fixed using a mounting belt that is extended from the bottom plate 210, the length of the attachment belt being adjustable.

Besides the surface fastener 212, a reference index 211 is provided on the surface of the bottom plate 210. The reference index 211 may be irregularities integrally formed with the bottom plate 210 or may be provided on the surface of the bottom plate 210 by printing or seal bonding. Further, it is sufficient that the reference index 211 has such a pattern that the user is able to recognize its direction against the bottom plate 210. In this example, as shown in FIG. 1, a triangle whose vertex angle is directed in the direction of the toe is employed.

It is assumed that the walking assistance apparatus 100 according to this embodiment is used by a plurality of users in turns, not by only one specific user. Therefore, the user who would like to use the walking assistance apparatus 100 performs an operation of adjusting the position of the foot that wears the cupsole 500 to the optimal position on the bottom plate 210 when the user starts using the walking assistance apparatus 100. Specifically, the position in the right-left direction is adjusted in such a way that the lower thigh 901 rubs against the joint mechanisms 310 and 320, the front-back position is adjusted in such a way that the joint axis of the ankle joint 903 matches the rotation axis of the joint mechanisms 310 and 320 as much as possible, and the position in the rotational direction is adjusted in accordance with the user's peculiarity such as whether he/she is pigeon-toed/duckfooted. Through these adjustment operations, the optimal position of the cupsole 500 is determined for each user.

However, the aforementioned adjustment operations are complicated and thus the user needs to spend a large amount of time before he/she can successfully start using the walking assistance apparatus 100. When these adjustment operations are required for each usage, this may cause a frequency with which the user uses the walking assistance apparatus 100 to be reduced. On the other hand, there is a demand that users who have the same foot size like to share the cupsole 500. When the cupsole 500 is shared among a plurality of users, it is required that the record for each user not be left directly in the cupsole 500.

Figure 2:
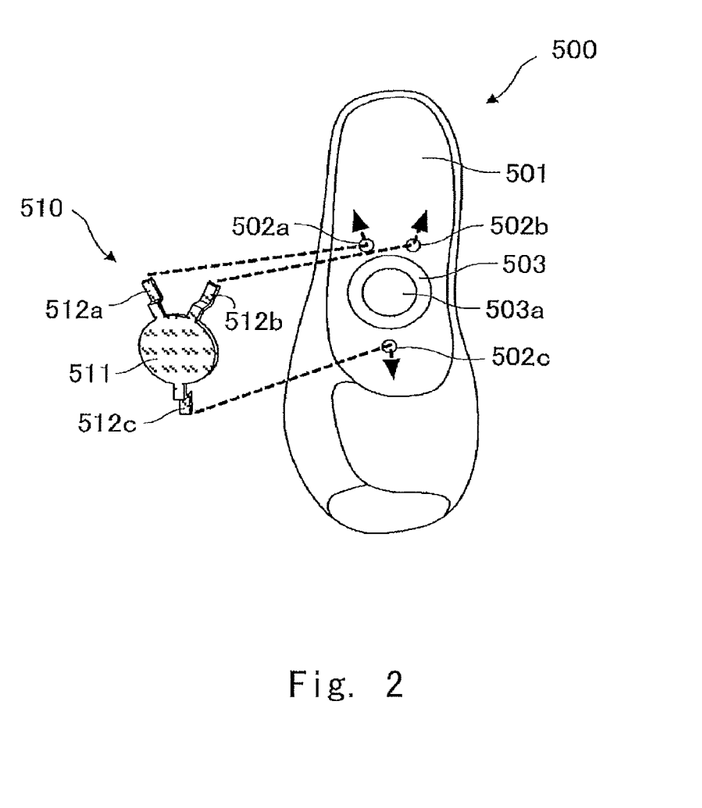
FIG. 2 is a diagram for describing a structure of the cupsole.

The cupsole 500 according to this embodiment that solves the aforementioned problems will be explained in detail. FIG. 2 is a diagram for describing the structure of the cupsole 500. The cupsole 500 according to this embodiment is mainly composed of a main body part 501 and an index member 510.

The main body part 501 is a shoe-shaped part on which the foot 902 is placed and in which the foot 902 is accommodated. A window frame 503 is embedded in a part of the main body part 501 that corresponds to the arch of the foot when the user places the foot 902 on the main body part 501. The window frame 503 has, for example, a disk shape formed of aluminum, and a window hole 503a that penetrates through the main body part 501 is provided at the center of the window frame 503.

The index member 510 is a member prepared for each user and can be attached to or detached from the main body part 501. The index member 510 is used in order to determine the attachment position with respect to the reference index 211 provided in the bottom plate 210, the attachment position varying for each user. When, for example, one main body part 501 is shared by ten users, ten index members 510 are prepared.

The index member 510 is formed by, for example, a transparent plastic plate. The index member 510 is formed of an index surface 511 that corresponds to the window frame 503 and has a circular shape, and three arm parts 512a, 512b, and 512c that are extended in the radial direction from the index surface 511. The three arm parts 512a, 512b, and 512c are flexible.

Each of the three arm parts 512a, 512b, and 512c serves as a mounting part with respect to the main body part 501. The main body part 501 includes mounting holes 502a, 502b, and 502c, each serving as a mounted part, that correspond to the three arm parts 512a, 512b, and 512c. Specifically, the arm part 512a is penetrated through the mounting hole 502a, the arm part 512b is penetrated through the mounting hole 502b, and the arm part 512c is penetrated through the mounting hole 502c. Then the tips of the respective arm parts that have penetrated through the mounting holes are bent and the bent tips are extended along the surface of the main body part 501 (in the example shown in FIG. 2, the surface which is opposite to the surface where the foot 902 is placed), whereby the index member 510 can be mounted on the main body part 501. That is, the arm part includes the penetrating part that penetrates through the mounting hole and the extended part at the tip side of the arm part that is extended along the surface of the main body part 501 after the penetrating part penetrates through the mounting hole. The penetrating part of the arm part determines the position of the index member 510 with respect to the main body part 501 and the extended part of the arm part stabilizes the mounting of the index member 510.

The three mounting holes 502a, 502b, and 502c are arranged around the window frame 503 in such a way that they become rotationally asymmetrical with one another. Therefore, the arm parts 512a, 512b, and 512c cannot be inserted into the mounting holes 502a, 502b, and 502c in combinations other than the given combination. That is, the user cannot mount the index member 510 on the main body part 501 in a wrong direction. The shape of the mounting holes 502a, 502b, and 502c may be circular or slit-like as long as the arm parts 512a, 512b, and 512c can be supported in a stable manner.

Further, the window hole 503a of the window frame 503 is smaller than the index surface 511 of the index member 510. Accordingly, the outer peripheral part of the index surface 511 can be placed on the window frame 503, and thus the index surface 511 becomes more stable. That the window hole 503a is smaller than the index surface 511 is particularly advantageous when a mark is formed on the index surface with a pen, as will be explained later. Further, when adhesive having adhesiveness of such a degree that it allows the index surface 511 to be peeled off from the window frame 503 is applied to the window frame 503, the index surface 511 can be cohesively supported on the window frame 503.

The window frame 503 may not be provided as a separate member and the window hole 503a may be directly provided in the main body part 501. By directly providing the window hole 503a in the main body part 501, the number of elements can be reduced and the manufacturing cost can be prevented from rising.

Figure 3:
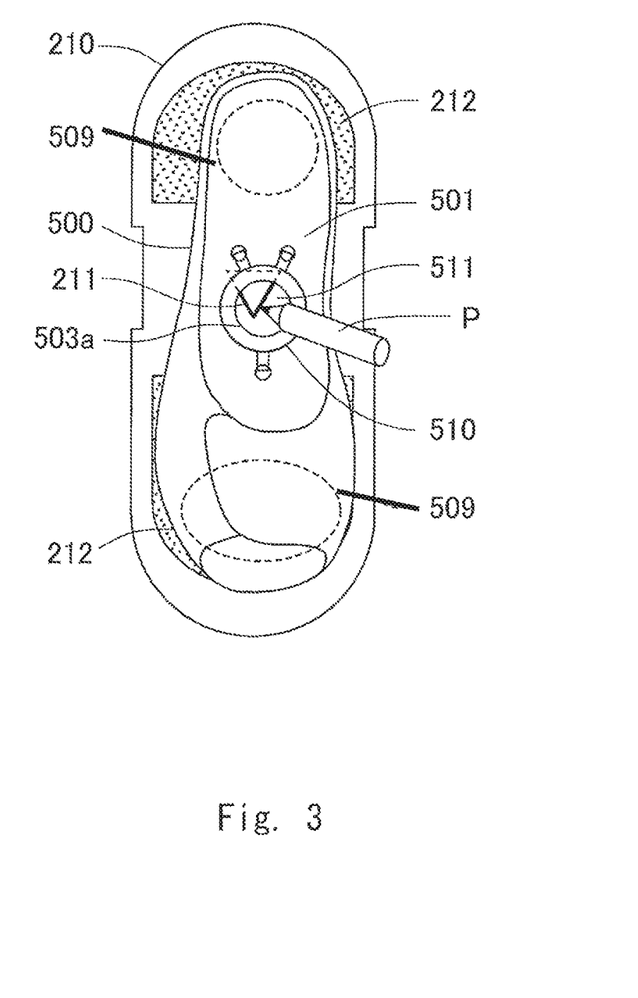
FIG. 3 is a diagram for describing a marking operation on an index member.

FIG. 3 is a diagram for describing a marking operation on the index member 510. When the user uses the walking assistance apparatus for the first time, the user first wears the cupsole 500 on which the brand-new index member 510 is mounted and adjusts the position of the cupsole 500 with respect to the bottom plate 210. As described above, since the surface fastener 509 is bonded to the rear surface of the cupsole 500, the user determines the optimal position of the cupsole 500 by repeatedly attaching the surface fastener 509 to or detaching the same from the surface fastener 212 bonded to the surface of the bottom plate 210.

When the optimal position of the cupsole 500 is determined, the foot 902 is pulled out while keeping the cupsole 500 fixed to the bottom plate 210. The reference index 211 is provided in such a position that at least a part of it can be visually recognized from the index surface 511 even when any user adjusts the position of the cupsole 500. In other words, the index surface 511 and the window hole 503a have such a size that at least a part of the reference index 211 can be visually recognized even when any user adjusts the position of the cupsole 500.

Next, the user forms a mark on the transparent index surface 511 with a pen P along the reference index 211 that has been visually recognized. The mark formed with the pen P may be a straight line that overlaps the outer periphery of the reference index 211 as shown in FIG. 3 or the inner part of the mark may be blacked out. At any rate, any mark will be fine as long as the relative positional relation of the cupsole 500 with the reference index 211 becomes clear. The mark may not be formed by the pen P and a seal may be bonded. That is, the mark may have any form as long as the relative positional relation of the cupsole 500 can be marked on the index surface as an index.

Figure 4:
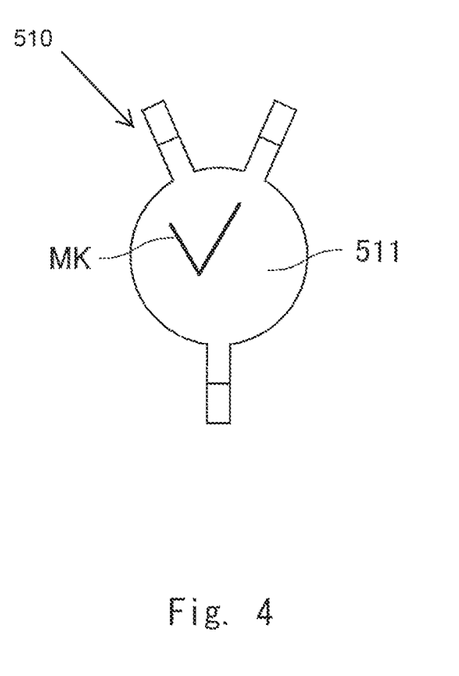
FIG. 4 is a diagram for describing the index member after the marking.

FIG. 4 is a diagram for describing the index member 510 after the marking. The personal index MK written in the index surface 511 is a user-specific index. Accordingly, the user or an operator manages the index member 510 on which the mark is formed separately from another user's. As a matter of course, matters required for the management may be recorded in the index member 510. For example, a bar code or the like may be printed in advance and information indicating the user who owns the index member 510 may be managed by a PC or the like.

In this embodiment, the index member 510 is formed by a transparent plastic plate, as described above. However, as long as the marking operation can be performed by causing the index member 510 to overlap the reference index 211 or the adjustment operation for causing the personal index MK to overlap the reference index 211 can be performed as will be described later, it is sufficient that the index member 510 has such a transparency that it can visually recognize the reference index 211 through the index surface 511. That is, the index surface 511 may not be colorless, or the arm parts 512a, 512b, and 512c may not be translucent members. The index surface 511 and the arm parts 512a, 512b, and 512c may be integrated with each other after they are formed of separate members.

Figure 5:
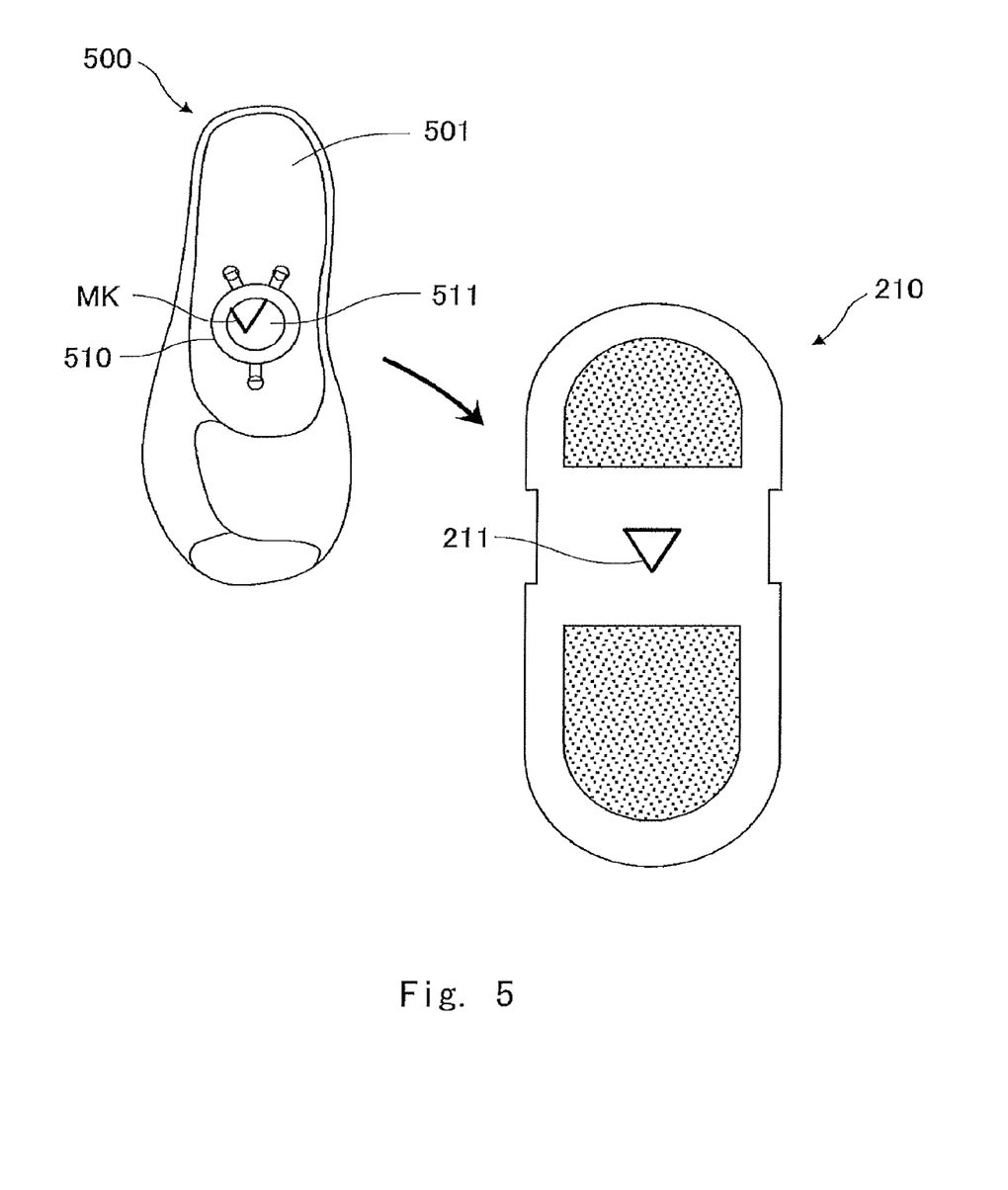
FIG. 5 is a diagram for describing a second or subsequent adjustment operation.

FIG. 5 is a diagram for describing an adjustment operation when the user uses the walking assistance apparatus 100 for a second or subsequent times. When the user uses the walking assistance apparatus 100 for the second or subsequent times, the user first mounts the index member 510 of his/her own used when the user performed the marking operation for the first time on the main body part 501 to complete the cupsole 500. Then the cupsole 500 is placed on the bottom plate 210 in such a way that the personal index MK of the index surface 511 and the reference index 211 of the bottom plate 210 overlap each other. Through the two stages of adjustment operations, the cupsole 500 is fixed to the bottom plate 210 at an optimal position. The user is able to start using the walking assistance apparatus 100 by just putting the foot 902 into the cupsole 500 and mounting other mounting tools thereon. It is not necessary that the main body part 501 used when the marking operation was performed be used as the target on which the index member 510 is mounted. It is instead sufficient that the main body part 501 of the same type and the same size as that used when the marking operation was performed be used in the cupsole 500.

As described above, when the user uses the walking assistance apparatus 100 for the second and subsequent times, the operation of adjusting the cupsole 500 with respect to the bottom plate 210 at the optimal position can be greatly reduced compared to that of related art. It is therefore possible to reduce the time required to start using the walking assistance apparatus 100. This causes a user's psychological barrier when he/she uses the walking assistance apparatus 100 to be reduced, whereby it is possible to improve the user's motivation for rehabilitation and the like. Further, since only the index member 510 is owned by each user, the users having the same foot size can share the cupsole 500. According to this sharing way, there is no need to directly leave the record of each user in the cupsole 500 that is shared by the users. Further, the index member 510 having a small size and a simple structure may be owned by each user, whereby it is possible to prevent the rising of the overall management cost and supplying cost required for the operation of the walking assistance apparatus 100.

In this example, when the index member 510 is mounted on the main body part 501, the index surface 511 is arranged on the surface of the main body part 501 on which the foot 902 is placed (inner surface) and the extended parts of the arm parts are extended along the opposite surface (outer surface). However, the index surface 511 may be arranged in such a way that it is extended along the outer surface of the main body part 501 and the extended parts of the arm parts may be led to the inner surface of the main body part 501.

Figure 6:
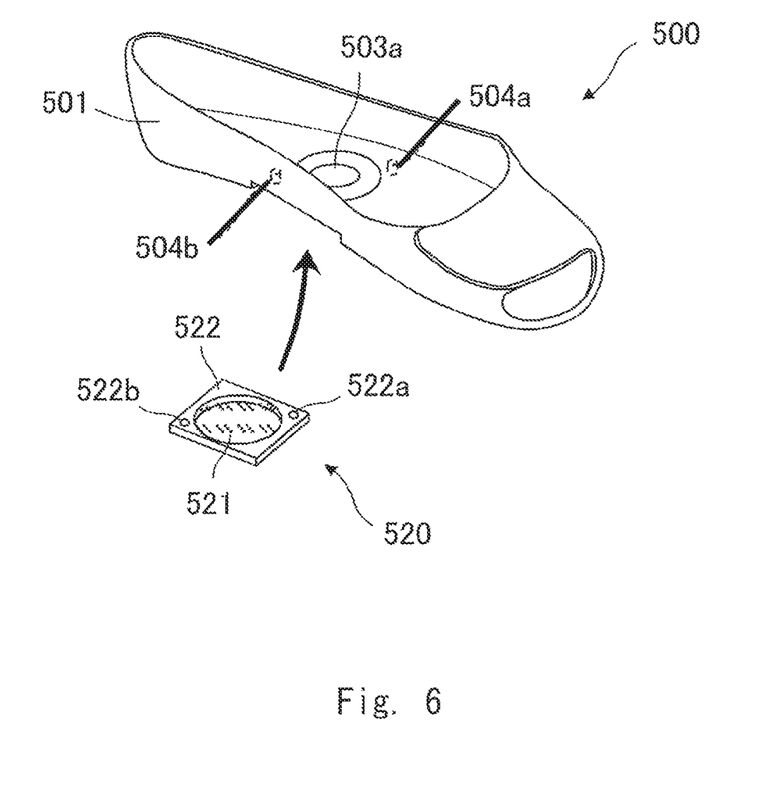
FIG. 6 is a diagram for describing another example.

Next, some other examples will be explained. In the following examples, the differences with the aforementioned example will be mainly explained. Description of structures similar to those in the aforementioned example will be omitted unless otherwise mentioned. FIG. 6 is a diagram for describing a first other example. An index member 520 according to this example includes a base plate 522 having a central part in which a fitting hole 522a is provided, and a transparent plate 521 fitted into the fitting hole 522a.

The transparent plate 521 serves a function of the index surface 511 in the aforementioned example and is formed of, for example, transparent plastic. The transparent plate 521 has such an area that it covers the window hole 503a of the cupsole 500, similar to the index surface 511, and the user is able to mark the personal index.

The base plate 522 includes fitting holes 522a and 522b that serve as mounting parts around the transparent plate 521. On the rear surface side of the main body part 501 of the cupsole 500 that is opposite to the placement surface on which the foot 902 is placed, projections 504a and 504b are installed as mounted parts. That is, the user is able to mount the index member 520 on the main body part 501 by fitting the projection 504*a* into the fitting hole 522*a* and fitting the projection 504*b* into the fitting hole 522*b*.

The main body part 501 may have a rear surface side in which a depression conforming to the outer shape of the index member 520 is provided. By accommodating the index member 520 in this depression, the user's feeling of strangeness at the time of walking can be reduced. Further, by making the shape of the depression and the positions where the projections and the fitting holes are arranged rotationally asymmetrical, it is possible to prevent the index member 520 from being mounted on the main body part 501 in a wrong direction.

Further, since the index member 520 is mounted on the outer surface side of the main body part, the index member 520 is not in direct contact with the user's foot. This structure is advantageous in terms of promoting better hygiene and reducing a psychological burden when, in particular, for example, another person manages the index member 520.

Figure 7:
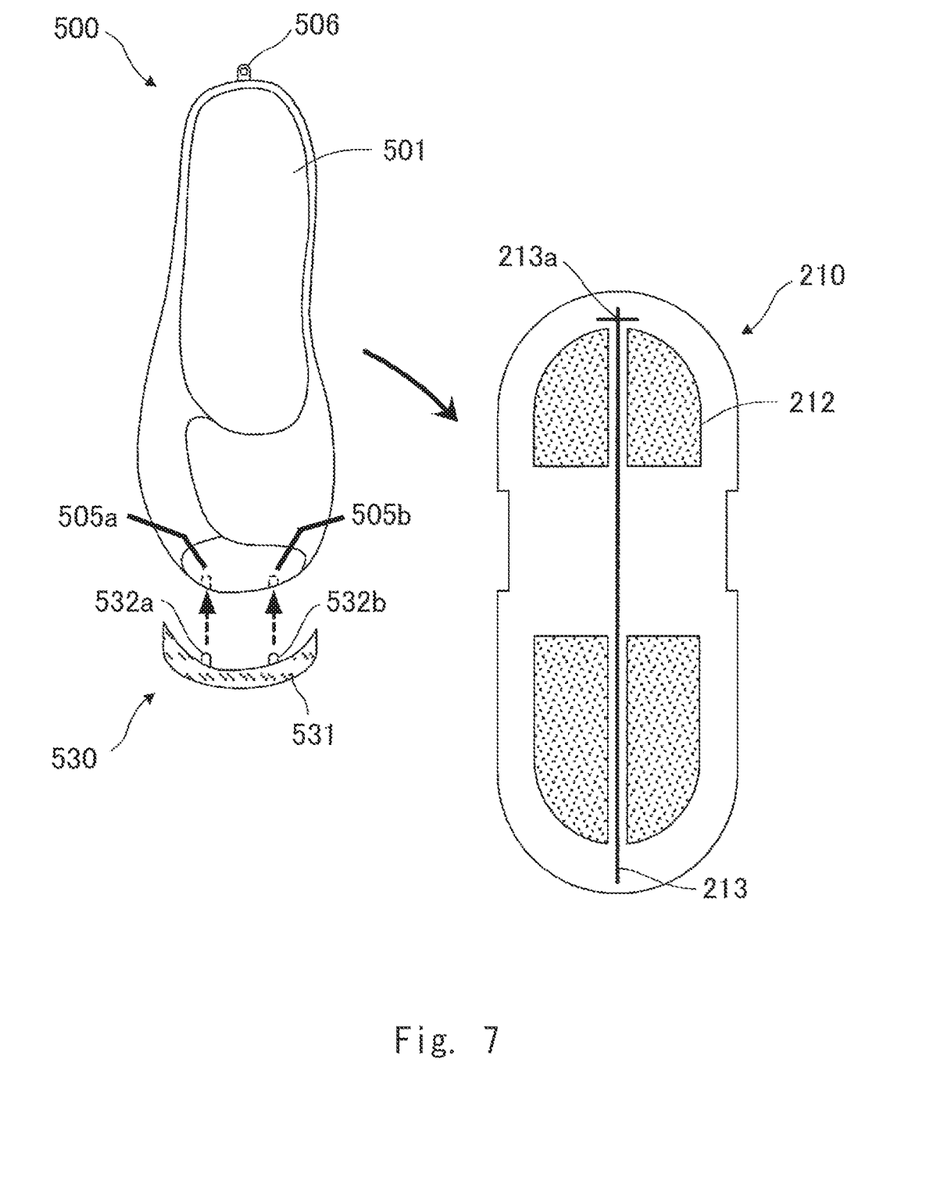
FIG. 7 is a diagram for describing still another example.

FIG. 7 is a diagram for describing a second other example. The index members 510 and 520 according to the aforementioned examples are mounted on the part near the arch of the foot 902 when the user wears the cupsole 500. Even when some irregularities are generated due to the mounting of the index members 510 and 520, the user does not have a strong feeling of strangeness as long as the irregularities are generated near the arch of the foot.

The cupsole 500 according to the second other example has a structure in which an index member 530 is mounted on the outer peripheral part of the main body part 501. When the index member 530 is mounted on the outer peripheral part of the main body part 501, the user does not perceive the presence of the index member 530. In this example, the index member 530 is mounted on the tip part of the main body part 501.

The index member 530 is formed of a transparent block 531 conforming to the shape of the tip of the main body part 501 and projections 532*a* and 532*b* that are inserted into fitting holes 505*a* and 505*b* as the mounted parts provided at the tip of the main body part 501. The transparent block 531 has functions similar to those of the index surface 511 in the aforementioned example, and is formed of, for example, transparent plastic. The user is able to mark the personal index on the transparent block 531.

The main body part 501 includes a heel part in which a reference protruding part 506 that is protruded in the outer peripheral direction is provided. The reference protruding part 506 is an index to match a reference point 213*a* of a reference index 213. In this example, the reference index 213 is expressed by the straight line that is extended from the heel part to the tip part of the bottom plate 210 and a straight line that is perpendicular to the above straight line in the vicinity of the heel. The point at which the two lines are perpendicular to each other is represented by the reference point 213*a*.

Figure 8:
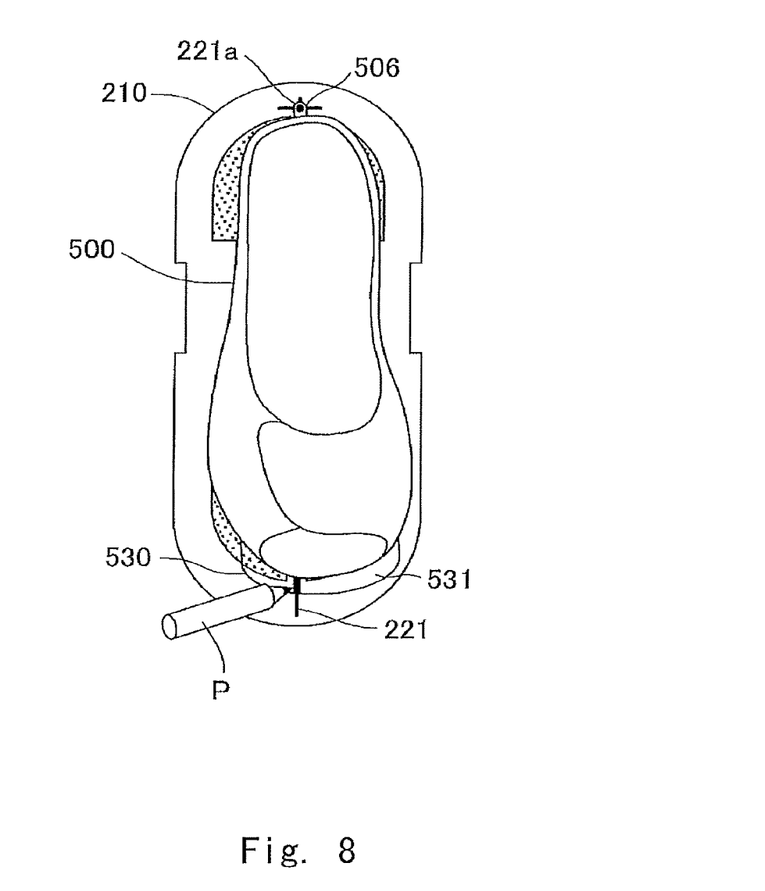
FIG. 8 is a diagram for describing a marking operation according to the other example.

FIG. 8 is a diagram for describing a marking operation with respect to the index member 530. When the user uses the walking assistance apparatus for the first time, the user first wears the cupsole 500 on which the brand-new index member 530 is mounted and adjusts the position of the cupsole 500 with respect to the bottom plate 210. The operations required to determine the optimal position of the cupsole 500 are performed by trial and error, similar to those in the first example. In this example, however, the reference protruding part 506 provided at the heel of the cupsole 500 matches the reference point 213*a* of the reference index 213.

After the optimal position of the cupsole 500 has been determined, the user forms a mark on the transparent block 531 with the pen P along the straight line of the reference index 213 that has been visually recognized. The mark may not be formed with the pen P and a seal may instead be bonded. That is, any mark will be fine as long as the relative positional relation is marked on the transparent block 531 as an index. In this case, the user is able to perform the marking operation even when the user does not pull out his/her foot 902 from the cupsole 500.

When the user uses the walking assistance apparatus for the second and subsequent times, after the index member 530 is mounted on the main body part 501, the reference protruding part 506 is made to match the reference point 213*a* and the personal index of the transparent block 531 is made to match the straight line of the reference index 213, whereby the position adjustment operation is completed. Since only one reference point 213*a* that matches the reference protruding part 506 is provided in the examples shown in FIGS. 7 and 8, only the position in the rotational direction of the cupsole 500 with respect to the bottom plate 210 can be adjusted. However, by providing a plurality of reference points of the bottom plate 210 and storing at which reference point the first position adjustment operation has been performed in the transparent block 531, the position of the cupsole 500 with respect to the bottom plate 210 can be adjusted also in the front-back direction and the right-left direction.

While the combination of the arm parts and the holes and the combination of the fitting holes and the projections have been explained as the structures of the mounting parts and the mounted parts in the aforementioned examples, the structures of the mounting parts and the mounted parts are not limited to these examples. In order to fix the mounting parts and the mounted parts more firmly, a combination of a screw with a screw hole may be used. In order to allow one of them to be attached to or detached from the other one of them, a snap with a protrusion and a recess may be used.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking assistance apparatus that assists a motion of a leg part of a user, the walking apparatus comprising:
 a foot sole plate; and
 a cupsole that configured to be worn by a user of a plurality of users and is fixed to the foot sole plate at an attachment position, the attachment position varying for each user, the cupsole including:
  a main body part configured to receive a foot of the user of the plurality of users; and
  an index member that is fixed to the main body part and is configured to determine the attachment position with respect to a reference index provided in the foot sole plate,
 wherein the index member is configured to be attached to or detached from the main body part,
 wherein the index member is a translucent member on which the user of the plurality of users is able to mark an own personal index with respect to the reference index,
 wherein the index member comprises two or more mounting parts to be mounted on the main body part, wherein the main body part includes mounted parts that correspond to respective mounting parts, wherein the mounting parts and the mounted parts are arranged in such a way that the index member cannot be mounted on the main body part by combinations other than a given combination, the mounting part and the mounted parts being respectively arranged at rotationally asymmetric positions, wherein the mounting parts each include an arm part that is extended from an index surface of the index member, wherein the mounted parts each include a hole part through which the arm part penetrates, wherein the index surface of the index member presents a circular shape, and the arm part extends in a radial direction from the index surface of the index member, and wherein the main body part is able to be fixed at an optimum position with respect to the foot sole plate for each user of the plurality of users by fixing the main body part to the foot sole plate so that the own personal index marked on the index member and the reference index provided on the foot sole plate overlap.

2. The walking assistance apparatus according to claim 1, wherein the arm part comprises a penetrating part that penetrates through the hole part and an extended part that is extended along a surface of the main body part after the penetrating part penetrates through the hole part.

3. The walking assistance apparatus according to claim 1, wherein the main body part includes a window part that is smaller than an index surface provided in a position of the main body part that corresponds to an index surface of the index member.

4. The walking assistance apparatus according to claim 1, wherein the index member is provided in the part of the main body part that corresponds to an arch of the foot.

5. The walking assistance apparatus according to claim 1, wherein the index surface of the index member is provided so as to be extended along an outer surface of the main body part, which is opposite to an inner surface of the main body part configured to receive the foot of the user of the plurality of users.

6. The walking assistance apparatus according to claim 1, wherein the index member is provided in an outer peripheral part of the main body part.

7. A cupsole attaching method for attaching a cupsole worn by a user of a plurality of users to a walking assistance apparatus that assists a motion of a leg part of the user of the plurality of users, an attachment position of the cupsole varying for each user of the plurality of users, the cupsole attaching method comprising:

adjusting a position of the cupsole on which an index member formed of a translucent member is mounted with respect to a reference index provided in a foot sole plate of the walking assistance apparatus;

marking an own personal index that matches the reference index on the translucent member after the position of the cupsole is adjusted;

and when the user of the plurality of users uses the walking assistance apparatus after marking the own personal index, mounting the translucent member on the cupsole by matching the own personal index to the reference index to determine the attachment position, thereby attaching the cupsole on which the translucent member has been mounted in the mounting step to the foot sole plate.

* * * * *